United States Patent [19]

Grinev et al.

[11] 3,968,237
[45] July 6, 1976

[54] LOCAL ANAESTHETIC

[76] Inventors: Alexei Nikolaevich Grinev, ulitsa Volgina, 15, korpus 2, kv. 57, Moscow; Alexandr Alexandrovich Stolyarchuk, ulitsa R. Ljuxemburg, 1, kv. 12, Vinnitsa; Pavel Alexandrovich Galenko-Yaroshevsky, ulitsa Kosmonavtov, 52, kv. 14, Vinnitsa; Vladimir Spiridonovich Tantsjura, ulitsa Litvinenko, 2, kv. 5, Vinnitsa; Natalya Vitalievna Arkhangelskaya, Krasnoprudnaya ulitsa, 26, kv. 36, Moscow, all of U.S.S.R.

[22] Filed: Apr. 9, 1974

[21] Appl. No.: 459,418

[30] Foreign Application Priority Data
  Apr. 13, 1973   U.S.S.R. ............................. 1912333

[52] U.S. Cl. ............................................... 424/285
[51] Int. Cl.² ........................................... A61K 31/34
[58] Field of Search ................................... 424/285

[56] References Cited
  OTHER PUBLICATIONS
Chemical Abstracts 59:7466(b) 1963.

Primary Examiner—Jerome D. Goldberg

[57] ABSTRACT

A local anaesthetic, comprising a salt of 2-methyl-3-carbethoxy-4-chloro-5-hydroxy-6-dimethylaminomethylbenzofuran, such as a tartrate salt, and a pharmaceutical solvent, such as water. The level of said compound in solutions amounts to from 0.25 to 1 percent by weight.

3 Claims, No Drawings

LOCAL ANAESTHETIC

The present invention relates to local anaesthetics.

Novocaine has gained wide popularity as a local anaesthetic in medical practice. However, Novocaine is not anaesthetically active enough and its effect is too shortlived.

It is an object of the present invention to provide a novel local anaesthetic superior to Novocaine in terms of activity and duration of the effect produced thereby.

This object is attained by the provision of a novel local anaesthetic which, in accordance with the invention, comprises an effective quantity of a compound of 2-methyl-3-carbethoxy-4-chloro-5-hydroxy-6-dimethylaminomethylbenzofuran in the form of a salt and a pharmaceutical solvent.

A preferred pharmaceutical solvent is water.

The concentration of the active principle, a salt of 2-methyl-3-carbethoxy-4-chloro-5-hydroxy-6-dimethylaminomethylbenzofuran, in solutions amounts to from 0.25 to 1 percent by weight. It is preferred that tartrate salt solutions of said compounds should be employed.

The preparation of the invention has been given a tentative name, and hereinafter may be called "Furocaine".

We have discovered that Furocaine exhibits a high level of anaesthetizing activity and is far superior to Novocaine in terms of depth and duration of its effect in infiltration, conduction and spinal forms of anaesthesia. Guinea pigs tested according to Bulbring-Wajda Furocaine produced a marked infiltration anaesthetic effect. When administered at concentrations of 0.05, 0.1 and 0.25 percent, Furocaine caused a total loss of sensitivity for periods of 15 to 20, 40 to 45 and 120 minutes, respectively. Novocaine has no anaesthetic effect at a concentration of 0.05 percent,; and at a concentration of 0.1 percent it caused a partial loss of sensitivity; a 0.25 percent Novocaine solution produced an anaesthetic effect which lasted from 8 to 14 minutes. At a concentration of 0.5 percent, Furocaine produced an anaesthetic effect lasting from 15 to 18 hours; a 1 percent Furocaine solution anaesthetized guinea pigs for from 24 to 30 hours, whereas Novocaine at the same concentrations produced an anaesthetic effect lasting from 15 to 20 and from 40 to 35 minutes, respectively.

In experiments on non-narcotized rabbits using what is known as the "painful" method, Furocaine caused a partial loss of sensitivity with a concentration of 0.05 percent for from 14 to 25 minutes; at a concentration of 0.1 percent for from 28 to 39 minutes; and at concentrations of 0.25, 0.5 and 1 percent Furocaine induced a total loss of sensitivity for from 79 to 114, 145 to 156 and 172 to 235 minutes, respectively. Under the same experimental conditions, Novocaine caused an incomplete loss of sensitivity at concentrations of 0.1, 0.25, 0.5 and 1 percent for from 7 to 11, 29 to 34, 40 to 53 and from 58 to 69 minutes, respectively.

In conduction anaesthesia experiments on rabbits, Furocaine produced full anaesthetic effect at a concentration of 0.25 percent for from 72 to 90 minutes, at a concentration of 0.5 percent for 132 to 135 minutes, and at a concentration of 1 percent for from 157 to 174 minutes; whereas Novocaine administered in the form of 0.5 and 1 percent solutions produced an analgesic effect for from 31 to 41 and 48 to 54 minutes, respectively. Furthermore, at all the above concentrations, Furocaine caused total anaesthesia, whereas Novocaine only partial.

Comparison of the anaesthetic effects of Furocaine and Novocaine in spinal anaesthesia indicates that both analgised rats at a concentration of 5 percent. However, Furocaine caused an immediate total analgesia lasting from 66 to 76 minutes, whereas Novocaine has a partial analgising effect for from 14 to 16 minutes.

A group of 30 healthy human volunteers aged from 20 to 30 was used to evaluate the anaesthetic effect of Furocaine as against Novocaine. The preparations were administered intracutaneously in 1 ml amounts in the form of 1 percent solutions and subcutaneously in 2 ml amounts in the form of 0.25 percent solutions. Both preparations were administered simultaneously at the flexion surfaces of the subjects' forearms. Administered subcutaneously, Furocaine produced an analgesic effect lasting 90 minutes on the average, whereas Novocaine analgised the subjects for only 15 minutes. Administered intracutaneously, Furocaine and Novocaine analgised the subjects for 90 and 12 minutes respectively.

Furocaine was employed so as to anaesthetize animals (rabbits and dogs) subjected to surgery: amputation of the hind limbs and resection of part of the small intestine. The analgesic effect was total and set in rapidly. In all cases use was made of a 0.25 percent solution of Furocaine administered in a single dose at the rate of from 20 to 80 ml. No side effects were observed either during surgery or in the immediate postoperative period. The surgical wounds invariably healed by primary tension; the postoperative period was marked by no complications.

Furocaine exhibits a low level of toxicity. Its DMT is 90 mg/kg in a single intravenous injection, 200 mg/kg in intraperitoneal administrations, and 610 mg/kg in subcutaneous administration. Novocaine is somewhat more toxic.

The prolonged administration of Furocaine to rats, e.g. 10 days of subcutaneous injections in a dose of 20 mg/kg, caused no noticeable alterations in the exterior appearance or the behaviour of the animals; the histological structure of the animals' viscera was also not disturbed. No changes were evident in the histological structure of the skin and subcutaneous connective tissues at the sites of Furocaine administration. Furocaine did not affect the composition of the blood constituents, the serum proteins, or the cytochromoxidase and peroxidase activity in the granulocytes. Furocain does affect blood coagulability which, according to throboelastograms, rises for the first 1.5 to 2 hours after the preparation has been administered.

Apart from its local anaesthetic effect, Furocaine also has a mild sedative and ganglioblocking effect and boosts by from 20 to 30 percent the volumetric rate of the coronary blood flow in acute experiments on cats. Furocaine also has an antirhythmic effect, eliminating rhythm disturbances induced by strophantin, aconitine and calcium chloride. When administered in small doses, e.g. on the order of from 0.5 to 1 mg/kg, Furocaine slightly stimulates intestinal contractility, while higher doses of the preparation, e.g. up to 10 mg/kg, bring about manifestations of intestinal muscular atony.

Furocaine was found to stimulate the contractility of the isolated uterus of various kinds of experimental animals, with the guinea pig's uterus being the most sensitive thereto. In experiments on intact animals, the level of uterine sensitivity to Furocaine was found to depend on the particular oestral phase as well as on the species of the animal; here, too, guinea pigs showed the highest response to Furocaine stimulation.

Forocaine may be employed, in the form of a tartrate, e.g. for intracutaneous injections in 1 percent solutions of a 1 ml dose, subcutaneously in 0.25 percent solutions of a 2 ml dose, and otherwise similarly to Novocaine.

2-methyl-3-carbethoxy-4-chloro-5-hydroxy-6-dimethylaminomethylbenzofuran is a novel compound never mentioned hitherto by any author, and said compound was first synthesized in the form of a base. The said compound is produced in a process which comprises aminomethylating 2-methyl-3-carbethoxy-4-chloro-5-hydroxybenzofuran with bis(dimethylamino)methane or a mixture of Formalin with dimethylamine in an organic solvent inert to the parent components. The reaction may be carried out both at ambient and at an elevated temperature. When the reaction is complete, the desired product is recovered by adding water to the reaction solution, with the product precipitating as an easily recoverable base. The product base, 2-methyl-3-carbethoxy-4-chloro-5-hydroxy-6-dimethylaminomethylbenzofuran, is then reacted with an inorganic acid, e.g. hydrochloric, or an organic acid, e.g. tartaric acid, to be converted to the acid salt readily soluble in water. The resultant preparation is employed as a local anaesthetic in the form of solutions.

The practice of the process whereby the preparation of this invention is synthesized may be further understood by reference to the following specific example to wit:

EXAMPLE 1 a. A solution of 12.75 g of 2-methyl-3-carbethoxy-4-chloro-5-hydroxybenzofuran and 8 ml of bis(dimethylamino)methane in 75 ml of dry dioxane is refluxed with boiling for 6 hours, then cooled to 20°C and then poured into water. The precipitate is filtered off, washed with water and dried. The yield of 2-methyl-3-carbethoxy-4-chloro-5-hydroxy-6-dimethylaminomethylbenzofuran is 12.6 g (80.5%); m.p., 130°–131.5°C (from alcohol).

Actual composition, in %: C, 58.10; H, 5.97; N, 4.58; Cl, 11.26; $C_{15}H_{18}ClNO_4$ Estimated composition, in %: C, 57.79; H, 5.81; N, 4.49; Cl, 11.39.

b. A solution of 1.9 g of 2-methyl-3-carbethoxy-4-chloro-5-hydroxybenzofuran, 2.6 ml of a 33 percent aqueous solution of dimethylamine and 0.6 ml of 36 percent Formalin in 12 ml of dimethylformamide is refluxed at a temperature of 100° to 105° for 8 hours and then cooled to ambient temperature. The precipitated crystals are filtered off, washed with water and dried in order to yield 0.75 g of crystalline 2-methyl-3-carbethoxy-4-chloro-hydroxy-6-dimethylaminomethylbenzofuran. An additional 0.4 g of crystals is obtained from the parent solution by dilution with water. The total yield is 1.15 g (50%); m.p., 130°–131°C (from alcohol). Mixed melting of the product crystals with a specimen from Example 1a gave no depression of the melting point.

c. 2.6 g of tartaric acid in 25 ml of an alcohol is added with stirring to a solution of 10.1 g of 2-methyl-3-carbethoxy-4-chloro-5-hydroxy-6-dimethylaminomethylbenzofuran in an anhydrous organic solvent, e.g. ether. The precipitate is filtered off and recrystallized from alcohol. The yield of 2-methyl-3-carbethoxy-4-chloro-5-hydroxy-6-dimethylaminomethylbenzofuran tartrate is 10 g (80% of the theoretical); m.p., 164.5°–166°C.

Actual, in %: C, 53.02; H, 5.41; Cl, 9.13; $C_{15}H_{18}ClNO_4 \cdot \frac{1}{2} C_4H_6O_6$ Estimated, in %: C, 52.78; H, 5.48; Cl, 9.18.

What is claimed is:

1. A local anaesthetic composition comprising an amount sufficient to produce a local anaesthetic effect of 2-methyl-3-carbethoxy-4-chloro-5-hydroxy-6-dimethylaminomethylbenzofuran in the form of a salt selected from the group consisting of the tartaric and hydrochloric acid salts and in a pharmaceutically acceptable aqueous solvent.

2. The anaesthetic composition as claimed in claim 1, which comprises 2-methyl-3-carbethoxy-4-chloro-5-hydroxy-6-dimethylaminomethylbenzofuran tartrate.

3. The local anaesthetic composition as claimed in claim 1, wherein the content of the salt of 2-methyl-3-carbethoxy-4-chloro-5-hydroxy-6-dimethylaminomethylbenzofuran is utilized in a concentration of from 0.25 to 1 percent by weight.

* * * * *